United States Patent [19]
Schnell

[11] Patent Number: 6,019,824
[45] Date of Patent: Feb. 1, 2000

[54] BUBBLE TRAP CHAMBER

[75] Inventor: William J. Schnell, Libertyville, Ill.

[73] Assignee: Medisystems Technology Corporation, Las Vegas, Nev.

[21] Appl. No.: 09/094,417

[22] Filed: Jun. 9, 1998

[51] Int. Cl.[7] .................................................. B01D 19/00
[52] U.S. Cl. ................................ 96/177; 96/195; 96/209; 210/188; 604/5; 604/406
[58] Field of Search ................................ 95/261; 96/177, 96/195, 208, 209, 216; 210/188; 604/4, 5, 126, 405, 406

[56] References Cited

U.S. PATENT DOCUMENTS

| | | | |
|---|---|---|---|
| 4,102,655 | 7/1978 | Jeffrey et al. | 210/188 |
| 4,345,919 | 8/1982 | Wilkinson et al. | 95/261 |
| 4,368,118 | 1/1983 | Siposs | 96/208 |
| 4,411,783 | 10/1983 | Dickens et al. | 210/304 |
| 4,662,906 | 5/1987 | Matkovich et al. | 210/188 |
| 4,690,762 | 9/1987 | Katsura | 210/436 |
| 4,743,371 | 5/1988 | Servas et al. | 210/188 |
| 4,919,802 | 4/1990 | Katsura | 96/209 |
| 4,964,984 | 10/1990 | Reeder et al. | 210/188 |
| 5,045,096 | 9/1991 | Quang et al. | 55/321 |
| 5,258,127 | 11/1993 | Gsell et al. | 210/188 |
| 5,312,479 | 5/1994 | Weinstein et al. | 96/209 |
| 5,328,461 | 7/1994 | Utterberg | 604/80 |
| 5,484,474 | 1/1996 | Weinstein et al. | 96/209 |
| 5,651,765 | 7/1997 | Haworth et al. | 210/188 |
| 5,674,199 | 10/1997 | Brugger | 604/4 |
| 5,707,431 | 1/1998 | Verkaart et al. | 96/177 |
| 5,849,065 | 12/1998 | Wojke | 95/261 |

OTHER PUBLICATIONS

Brochure by the Medisystems Corporation entitled: "Hemodialysis Blood Tubing Sets . . . Solutions for Today" 3 pages, no date.

*Primary Examiner*—Duane S. Smith
*Attorney, Agent, or Firm*—Gerstman, Ellis & McMillin, Ltd.

[57] ABSTRACT

A tubular set for the conveyance of blood includes flexible set tubing and a bubble trap chamber connected to the tubing for any desired extracorporeal blood transport process. The bubble trap chamber includes a housing defining an outer wall, a flow inlet to the interior of the housing, and a flow outlet at or near the bottom of the housing. The housing also includes an inner wall adjacent to its top. The inner wall is radially inwardly spaced from the outer wall within the chamber, extending circumferentially and generally parallel to the outer wall for at least about 90° of the circumference of the outer wall and preferably at least 180°, to define a circumferential passageway between the inner and outer walls. The flow inlet communicates with the circumferential passageway, so that blood can be directed to flow from the inlet horizontally and circumferentially through the passageway to a pair of passageway outlets. The passageway outlets are spaced in the chamber from the inlet, with the effect that the horizontal blood flow path of blood in the chamber is lengthened with less flow velocity, which improves the bubble removal capability of the bubble trap chamber.

20 Claims, 1 Drawing Sheet

BUBBLE TRAP CHAMBER

BACKGROUND OF THE INVENTION

Tubular sets for the conveyance and handling of blood in an extracorporeal manner generally have bubble trap chambers for the removal of air or other gas bubbles from the blood prior to placing the blood in a dialyzer or other device for processing of the blood, and also prior to returning blood back to the patient.

It is desirable for such bubble removing chambers to have the lowest possible volume, so that they hold a minimum amount of blood flowing through the circuit at any given time. At the same time, it is important for such bubble removing chambers to be very effective in their removal of bubbles even at the high flow rates (up to 500 ml min.) which are recently being used in blood treatment processes such as hemodialysis.

Thus, because of the need for effectiveness of bubble removal chambers at high flow rates, older designs of bubble removal chambers have been found to be deficient, allowing bubbles to pass back into the patient at higher flow rates than rates for which they were designed, or exhibiting undesirably high blood volumes. Preferably, blood volumes of 25 cc or less are desired.

By this invention, a new design of bubble trap chamber is provided which combines effective bubble removal even at high flow rates, coupled with a low blood volume, preferably of no more than 25 cc.

DESCRIPTION OF THE INVENTION

By this invention, a tubular set is provided for the conveyance of blood, typically between a patient and a blood processing device. The set comprises flexible set tubing and a bubble trap chamber which is connected to the tubing. Apart from the change in design of the bubble trap chamber, sets of conventional design may be used.

The bubble trap chamber comprises a housing which defines an outer wall, and a flow inlet to the interior of the housing. A flow outlet from the housing interior is also provided at or near the bottom of the housing, in position of use.

By this invention, the housing comprises an inner wall adjacent to the top of the housing. This inner wall is radially inwardly spaced from the outer wall, within the chamber. The inner wall extends circumferentially and generally parallel to the outer wall for at least about 90° of the circumference of the outer wall. Thus, a circumferential passageway is defined between the inner and outer walls.

Preferably, the outer wall and the circumferential passageway thus defined extends for at least about 180° of the circumference of the outer wall.

The flow inlet communicates with the circumferential passageway. Thus, blood is directed to flow from the inlet, horizontally and circumferentially through the passageway, to a passageway outlet which is spaced in the chamber from the flow inlet. The effect of this is to lengthen the horizontal flow path of blood in the chamber as it passes through the circumferential passageway for at least 90° and preferably 180 or more degrees of circumferential passage. During this horizontal flow, additional time is provided, compared with similar prior art bubble trap chambers, for bubbles to rise to the top of the chamber, augmented by the extended horizontal flow of the blood in the chamber. Then, blood passes out of the circumferential passageway into the main part of the chamber, and moves downwardly toward the bottom exit or flow outlet.

Thus, by this invention, a bubble trap chamber may be of the size and outer shape of conventional, prior art bubble trap chambers, but it exhibits a stronger, more effective bubble removal characteristic because of the lengthened horizontal flow path of blood in the chamber.

The housing of the chamber of this invention may be of circular cross section near its bottom, being proportioned in conventional manner to fit into conventional bubble detectors of commercially available hemodialysis machines. Thus, a conventional arterial or venous set for hemodialysis, for example, may be modified by the substitution of a bubble trap chamber in accordance with this invention, and used in accordance with what is presently conventional with respect to commercial hemodialysis machines, without any significant change except for the fact that better bubble removal is provided by the bubble trap chamber of this invention than with corresponding bubble trap chambers of the prior art.

It is also preferable for the housing of the bubble trap chamber of this invention to define a bottom wall for the circumferential passageway. The inner wall and circumferential passageway may connect with the flow inlet, which inlet preferably defines a vertical conduit having an aperture positioned to direct blood with horizontal flow into the circumferential passageway.

In one specific embodiment, the flow inlet is centrally spaced relative to the inner wall, so that the flow aperture connects with the circumferential passageway in a manner to provide bidirectional flow from the flow inlet through separate portions of the circumferential passageway. In this circumstance, each opposed end of the circumferential passageway from the flow inlet defines a separate passageway outlet. This bidirectional flow can reduce the horizontal blood flow velocity, for improved bubble removal.

DESCRIPTION OF SPECIFIC EMBODIMENTS

Figure 1:
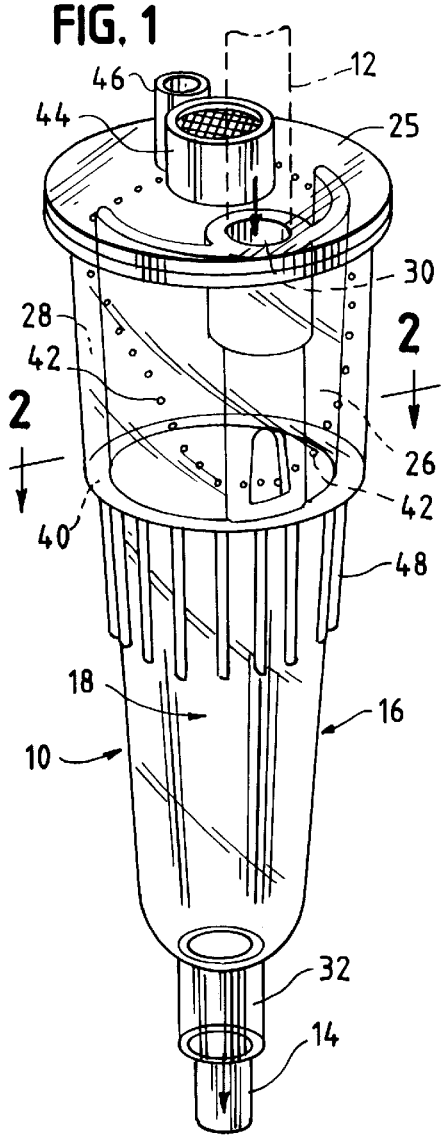
FIG. 1 is a perspective view of a tubular set which carries a bubble trap chamber in accordance with this invention, the tubular set being shown in highly fragmentary form.

Referring to the drawings, tube portions 12, 14 of a tubular set 10 for the conveyance of blood are shown to be connected to bubble trap chamber 16 as an inlet and an outlet for chamber 16, which is also part of set 10. Set 10 may comprise other components in a conventional manner for the receiving of blood and the transport thereof, typically between a patient and a blood processing device, for example a hemodialyzer or some other device for the treatment of blood. After such treatment, the blood is returned to the patient.

Bubble trap 16 comprises a housing 18, which defines an outer wall 20, as shown.

Figure 3:
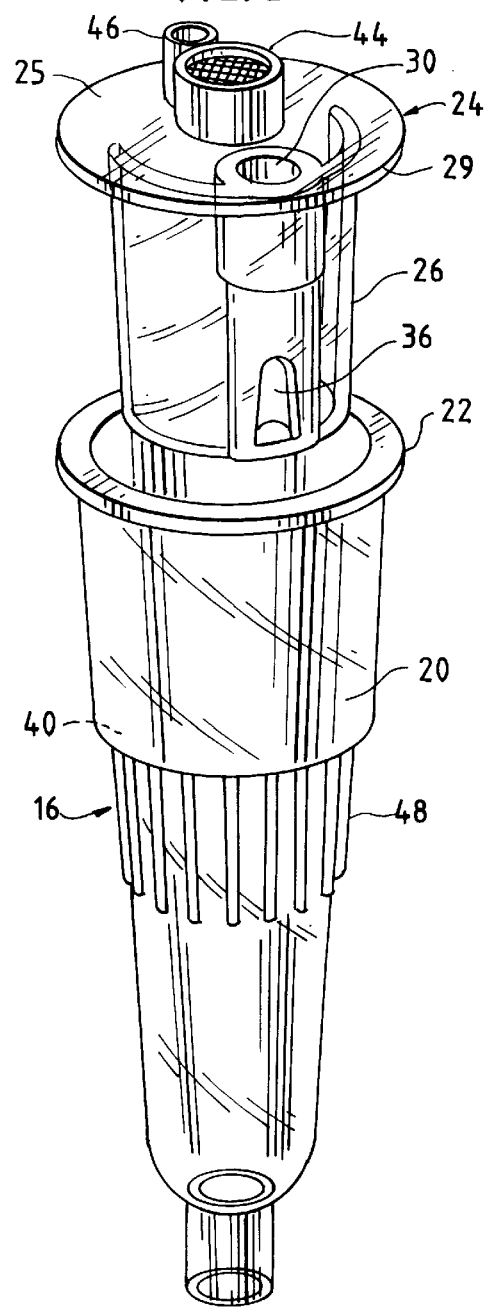
FIG. 3 is an exploded, perspective view of the bubble trap chamber of FIG. 1.

In this particular embodiment, as shown by FIG. 3, bubble trap chamber 16 is of substantially two-piece construction, comprising tubular outer wall 20 having an open end defined by flange 22, which receives a separately molded end portion 24 having an inner wall 26, spaced from outer wall 20 when installed. An upper flange 29 is provided, which can seal to flange 22 by RF sealing, heat sealing, adhesive, or the like. Thus, bubble trap chamber 10 and its housing 18 can be made primarily of two molded components 20, 24.

Bubble trap chamber 16 defines a flow inlet 30, which is connected to set tubing 12 in the set, and a flow outlet port tube 32, which is connected to set tubing 14 by solvent sealing or the like.

Figure 2:
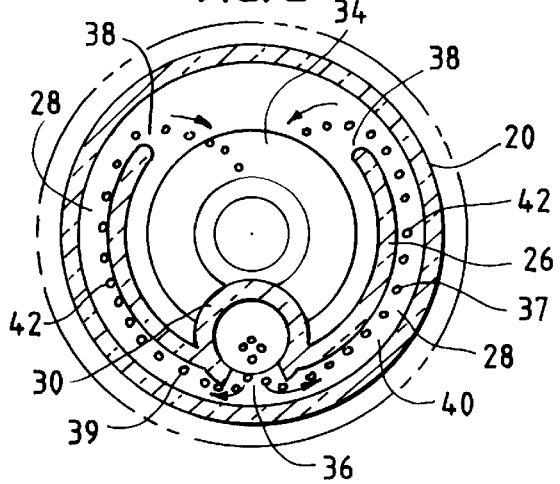
FIG. 2 is a sectional view taken along line 2—2 of FIG. 1.

When assembled as shown in FIGS. 1 and 2, inner wall 26, which is positioned adjacent to the top wall 25 of housing 18, is spaced radially inwardly from outer wall 20 within the chamber 34 defined by outer wall 20. Inner wall 26 is radially inwardly spaced from outer wall 20 within the chamber 34, extending circumferentially and generally parallel to outer wall 20 for a distance in this embodiment of more than 180° of the circumference of the outer wall, to define a circumferential passageway 28 between inner wall 26 and outer wall 20. Flow inlet 30 comprises a tube which extends axially downwardly from its connection point with set tubing 12 toward the bottom of inner wall 26, being integrally molded therewith if desired. An outwardly facing aperture 36 is provided at the bottom of inlet tube 30, to permit blood to flow in a horizontal direction from inlet tube 30 into circumferential passageway 28. Specifically, inlet tube 30 and aperture 36 are positioned at a midpoint of circumferential passageway 28, so that blood flow is bidirectional through two sections 37, 39 of the circumferential passageway 28, flowing to the respective ends 38 into the main part of chamber 34.

It can be seen that housing 20 defines an internal step in its diameter that defines an internal flange 40, against which the bottom of internal wall 26 abuts so that circumferential passageway 28 defines a floor. The top of passageway 28 is defined by the top wall 25 of chamber 16, to provide an enclosed area with generally horizontal flow of blood circumferentially inside of outer wall 20, which horizontal flow path for blood is not found in corresponding prior art bubble traps of similar shape. Thus, this added length of circumferential flow for blood provides added opportunity for air bubbles 42 found in the blood to rise upwardly toward the undersurface of end wall 25, to thus be collected for periodic removal through a conventional needle injection site 44 carried on top wall of chamber 16.

Blood which is passed through an end 38 of passageway 28 moves into main chamber 34, where it flows in a pattern similar to conventional bubble traps of similar design, moving downwardly to be removed from the outlet 32 through set tubing 14. By this, additional time is provided for the migration of bubbles upwardly toward the top of a chamber, because of the enlarged width of chamber 16 relative to the narrower width of the flow of blood being withdrawn through set tubing 14.

Accordingly, bubble trap chambers of this design, which may be added as a replacement to conventional bubble trap chambers of substantially similar exterior design, exhibit better bubble removing capability than the corresponding bubble trap chambers of the prior art, yet they can be used in the same hemodialysis devices as their predecessor bubble trap chambers.

Auxiliary or branch set tubing may be connected to port 46 for pressure sensing, the addition of heparin solution, or the addition of priming or other parenteral solution in generally conventional manner.

Ribs 48 are provided to facilitate the fit of the chamber into a conventional bubble detector apparatus, and may be omitted if appropriate.

The above has been offered for illustrative purposes only, and is not intended to limit the scope of the invention of this application, which is as defined in the claims below.

That which is claimed:

1. A tubular set for the conveyance of blood, which set comprises flexible set tubing and a bubble trap chamber connected to said tubing, said bubble trap chamber comprising a housing defining an outer wall, a flow inlet to the interior of said housing, and a flow outlet at or near the bottom of said housing, said housing comprising an inner wall adjacent to the top of said housing, said inner wall being radially inwardly spaced from said outer wall within said chamber and extending circumferentially and generally parallel to said outer wall for at least about 90° of the circumference of the outer wall, to define a circumferential passageway between the inner and outer walls, said flow inlet communicating with said circumferential passageway, whereby blood is directed to flow from said flow inlet horizontally and circumferentially through the passageway to at least one passageway outlet, which outlet is spaced in the chamber from said flow inlet, to lengthen the horizontal flow path of blood in said chamber.

2. The set of claim 1 in which said housing is of circular cross section near its bottom and proportioned to fit into conventional hemodialysis bubble detectors.

3. The set of claim 1 in which said housing defines a bottom wall for said circumferential passageway.

4. The set of claim 1 in which said inner wall and circumferential passageway extend for at least about 180° of the circumference of said outer wall.

5. The set of claim 1 in which said flow inlet defines an aperture positioned to direct blood with horizontal flow into said circumferential passageway.

6. The set of claim 1 in which said flow inlet is centrally spaced relative to said inner wall, for bidirectional flow from said flow inlet through said circumferential passageway, each end of the circumferential passageway defining a separate passageway outlet.

7. A tubular set for the conveyance of blood, which set comprises flexible set tubing and a bubble trap chamber connected to said tubing, said bubble trap chamber comprising a housing defining an outer wall, a flow inlet to the interior of said housing, and a flow inlet at or near the bottom of said housing, said housing being of circular cross section near its bottom and proportioned to fit into conventional hemodialysis bubble detectors, said housing comprising an inner wall adjacent to the top of said housing, said inner wall being radially inwardly spaced from said outer wall within said chamber and extending circumferentially and generally parallel to said outer wall for at least about 90° of the circumference of the outer wall, to define a circumferential passageway between the inner and outer walls, said flow inlet communicating with said circumferential passageway, and said housing also defining a bottom wall for said circumferential passageway, whereby blood is directed to flow from said inlet horizontally and circumferentially through the passageway to at least one passageway outlet, which is spaced in the chamber from said flow inlet, to lengthen the horizontal flow path of blood in said chamber.

8. The set of claim 7 in which said inner wall and circumferential passageway extend for at least about 180° of the circumference of said outer wall.

9. The set of claim 8 in which said flow inlet is centrally spaced relative to said inner wall, for bidirectional flow from said flow inlet through said circumferential passageway, each end of the circumferential passageway defining a separate passageway outlet.

10. The set of claim 9 in which said flow inlet defines an aperture positioned to direct blood with horizontal flow into said circumferential passageway.

11. A bubble trap chamber for use in the extracorporeal flow of blood, said bubble trap chamber comprising a housing defining an outer wall, a flow inlet to the interior of said housing, and a flow inlet at or near the bottom of said housing, said housing comprising an inner wall adjacent to the top of said housing, said inner wall being radially inwardly spaced from said outer wall within said chamber and extending circumferentially and generally parallel to said outer wall for at least about 90° of the circumference of the outer wall, to define a circumferential passageway between the inner and outer walls, said flow inlet communicating with said circumferential passageway, whereby blood is directed to flow from said inlet horizontally and circumferentially through the passageway to at least one passageway outlet, which outlet is spaced in the chamber from said inlet, to lengthen the horizontal flow path of blood in said chamber.

12. The bubble trap chamber of claim 11 in which said housing is of circular cross section near its bottom and proportioned to fit into conventional hemodialysis bubble detectors.

13. The bubble trap chamber of claim 11 in which said housing defines a bottom wall for said circumferential passageway.

14. The bubble trap chamber of claim 11 in which said inner wall and circumferential passageway extend for at least about 180° of the circumference of said outer wall.

15. The bubble trap chamber of claim 11 in which said flow inlet defines an aperture positioned to direct blood with horizontal flow into said circumferential passageway.

16. The bubble trap chamber of claim 11 in which said flow inlet is centrally spaced relative to said inner wall, for bidirectional flow from said flow inlet through said circumferential passageway, each end of the circumferential passageway defining a separate passageway outlet.

17. The bubble trap chamber of claim 11 in which said housing defines a bottom wall for said circumferential passageway, said inner wall and circumferential passageway extending for at least about 180° of the circumference of said outer wall.

18. The bubble trap chamber of claim 17 in which said flow inlet is centrally spaced relative to said inner wall, for bidirectional flow from said flow inlet through said circumferential passageway, each end of the circumferential passageway defining a separate passageway outlet.

19. The bubble trap chamber of claim 18 in which said housing is of circular cross section near its bottom and proportioned to fit into conventional hemodialysis bubble detectors.

20. The bubble trap chamber of claim 18 in which said flow inlet defines an aperture positioned to direct blood with horizontal flow into said circumferential passageway.

* * * * *